US00PP08147P

United States Patent [19]

Holtkamp, Sr.

[11] Patent Number: Plant 8,147

[45] Date of Patent: Feb. 16, 1993

[54] AFRICAN VIOLET PLANT NAMED RUMIKO

[76] Inventor: Reinhold Holtkamp, Sr., Blumenstrasse 28, D 4242 Rees-Haffen, Fed. Rep. of Germany

[21] Appl. No.: 736,502

[22] Filed: Jul. 26, 1991

[51] Int. Cl.[5] ..... A01H 5/00

[52] U.S. Cl. ..... Plt./69.2

[58] Field of Search ..... Plt./69.1, 69.2

*Primary Examiner*—James R. Feyrer

*Attorney, Agent, or Firm*—Foley & Lardner

[57] ABSTRACT

A new and distinct cultivar of African violet named Rumiko characterized by its single violet-shaped, purplish blue flowers; strong, upright flower stems that curve slightly toward the center to form a compact bouquet above the leaves; medium green, oval leaves; profuse flowering, vigorous and compact growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Rumiko.

The new cultivar was referred to during the breeding and selection process by the designation 800/20 and is a product of a planned breeding program. The new cultivar was originated from a cross made by me in the controlled breeding program in Haffen, Federal Republic of Germany. The female, or seed parent was a cultivar designated K 129/3. The male, or pollen parent was a cultivar designated I 102/6.

Rumiko was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Rumiko has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Rumiko, which in combination distinguish this African violet as a new and distinct cultivar:

1) Strong, upright flower stems curving slightly toward the center.

2) Single violet-shaped purplish blue flowers.

3) Profuse flowering.

4) Each plant carries 9–12 and more upright flower stems each of which carries 8–9 and more flowers.

5) Long lasting, non-dropping flowers.

6) Vigorous and compact grower.

7) Plant saleable 10 to 11 weeks after potting.

8) Seed capsules push slightly through.

9) Medium green, oval leaves.

10) After maturity the flowers dry off, and remain on the peduncle without becoming infected by botrytis.

Rumiko is similar in certain respects to Improved Iowa, disclosed in U.S. Plant Pat. No. 7,132. The purplish blue color of the blooms and the velvety, medium green foliage of Improved Iowa and Rumiko are similar. However, Rumiko has a darker shade of Violet-Blue Group 89 and the blooms have longer, less rounded petals than those of Improved Iowa. Also, in contrast to Rumiko, Improved Iowa has somewhat wavy blooms and often 1–2 additional very small petals in the center. Rumiko has more flower stems and more flowers per stem than Improved Iowa. Finally, Rumiko has oval leaves, whereas Improve Iowa has oval to heart-shaped leaves.

The accompanying color photographic drawing shows a typical specimen plant of the new cultivar. The colors appearing in the photograph are as true as possible with color illustrations of this type.

In the following description, color references are made to the Royal Horticultural Society Colour Chart (R.H.S.), except where general colors of ordinary signifance are referred to. Color values were taken under natural sunlight conditions at approximately 12 p.m. in Nashville, Tenn.

Botanical classification: *Saintpaulia ionantha,* Ramat., c.v. Rumiko.

Parentage:

*Male parent.*—I 102/6.

*Female parent.*—K 129/3.

Propagation: The new cultivar holds its distinguishing characteristics through successive propagations by leaf cuttings.

Plant: From 8 cm to 11 cm tall when grown in pots, and 23–28 cm in diameter when fully grown.

Leaves:

*General form.*—Oval.

*Diameter.*—55–60 mm wide and 65–70 mm long.

*Texture.*—Velvety.

*Aspect.*—Shiny, hairy.

*Veins.*—Upperside: visible; underside: well pronounced, light green or purplish red, shiny.

*Color (upperside).*—Yellow-Green Group 147 A.

*Color (underside).*—Greyed-Green Group 194 C to D.

*Petiole.*—Strong upright, brownish red, hairy.

Flowers:

*Buds.*—Bell-shaped, purplish, 5–7 mm just before opening.

*Sepals.*—Five (5). Color: Brownish green.

*Calyx.*—Shape: Funnel-shaped. Aspect: Spear-shaped, hairy.

*Peduncle.*—Character: Strong upright, hairy. Color: Green with purplish brown touch.

Individual flowers:

*Size.*—40–45 mm.

*Shape.*—Single violet-shaped.

*Color (upperside).*—Violet-Blue Group 89 A to B. Under cooler temperatures and more intensive lighting, the purplish blue tends to intensify.

*Color (underside).*—Violet-Blue Group 89 B to C.

*Borne.*—Each flower stem carries 8–9 and more flowers on strong, upright peduncles that are free standing above the leaves, thereby forming a compact bouquet.

*Flowering habit.*—Flowers 10–11 weeks after potting.

Reproductive organs:

*Stamens.*—Two (2). Anthers: 2 composed of 4 anther cells, seed capsules push slightly through.

*Filaments.*—Yellowish green with purplish blue touch, 3–4 mm long.

*Pollen color.*—Yellow Group 7 A.

*Styles.*—5–7 mm long, purplish blue, base of ovary light green and hairy.

Roots: Normally developed, white when young, turning slightly brownish when older.

Disease resistance: Up to date, Rumiko has shown very good resistance to all major violet diseases.

GENERAL OBSERVATIONS

Rumiko is an attractive, vigorous grower with medium green, oval leaves. A tight bouquet of flowers free standing above the leaves develops after 10–11 weeks. Each of the 9–12 and more strong flower stems carries 8–9 and more single, violet-shaped purplish blue flowers contrasting nicely with the bright yellow anthers. The flowers are long-lasting and non-dropping and the seed capsules push slightly through.

I claim:

1. A new and distinct cultivar of African violet named Rumiko, as described and illustrated, and particularly characterized by its single violet-shaped, purplish blue flowers; strong, upright flower stems that curve slightly toward the center to form a compact bouquet above the leaves; medium green, oval leaves; profuse flowering, vigorous and compact growth habit, flowering 10–11 weeks after potting, and its long lasting and non-dropping flowers.

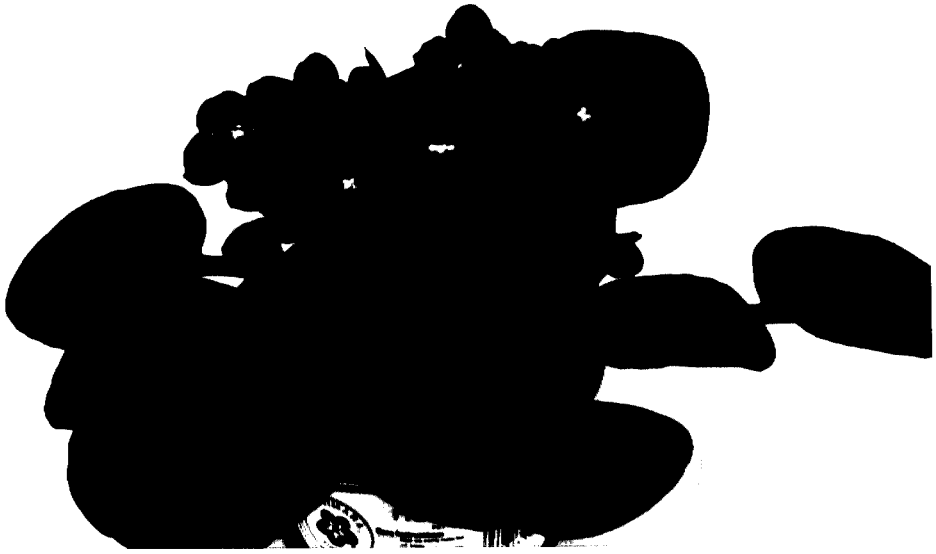

* * * * *